United States Patent [19]

Biggs et al.

[11] 4,447,725
[45] May 8, 1984

[54] QUANTITATIVE MEASUREMENT OF FAT, PROTEIN AND LACTOSE IN DAIRY PRODUCTS

[76] Inventors: Delmar A. Biggs, R.R. #3, Guelph, Ontario, Canada, N1H 6H9; John Shields, 23 North La., Wheldrake Nr. York, England

[21] Appl. No.: 273,392

[22] Filed: Jun. 15, 1981

[51] Int. Cl.$^3$ ............................................. G01J 1/00
[52] U.S. Cl. .................................. 250/339; 250/340; 250/343
[58] Field of Search ............... 250/338, 339, 340, 341, 250/343

[56] References Cited

U.S. PATENT DOCUMENTS

| | | | |
|---|---|---|---|
| 3,161,768 | 12/1964 | Goulden | 250/339 |
| 3,803,384 | 4/1974 | Braunlich | 250/338 |
| 4,076,983 | 2/1978 | Hopkins et al. | 250/341 |
| 4,247,773 | 1/1981 | Nexo et al. | 250/339 |
| 4,310,763 | 1/1982 | Shields | 250/339 |

FOREIGN PATENT DOCUMENTS 52-52694  4/1977  Japan .

OTHER PUBLICATIONS

Keeney, *Estimating the Average Carbon Chain Length of Saturated Fatty Acid Esters by Infrared Spectroscopy*, J. Amer. Oil Chem. Soc., 39, 304–305 (1962).

Smith, *Fatty Acid Composition of the Phospholipids and Other Lipids in Milk*, J. Dairy Sci., 45, 581–588 (1962).

Shields, *The Analysis of Milk by Infrared Absorption* (1975).

Primary Examiner—Davis L. Willis
Attorney, Agent, or Firm—Barnes, Kisselle, Raisch, Choate, Whittemore & Hulbert

[57] ABSTRACT

Electro-optical apparatus for measurement of fat, protein, lactose and solids in milk wherein a milk sample in a test cell is irradiated with reference and measurement beams at differing wavelengths for fat, protein and lactose, and signals are stored indicative of uncorrected concentrations. A scaling and correction circuit includes cross-correction circuitry for compensating the effects on each reading caused by the other constituents. The signals so corrected are then provided in percentage by weight or weight over volume on suitable digital displays. For enhanced accuracy of fat concentration, infrared absorption is measured at both the carbon-hydrogen stretching wavelength (3.48 microns) and the wavelength of absorption at the ester linkages (5.72 microns), and the resulting readings are combined in a predetermined function for obtaining a reading of fat concentration.

7 Claims, 6 Drawing Figures

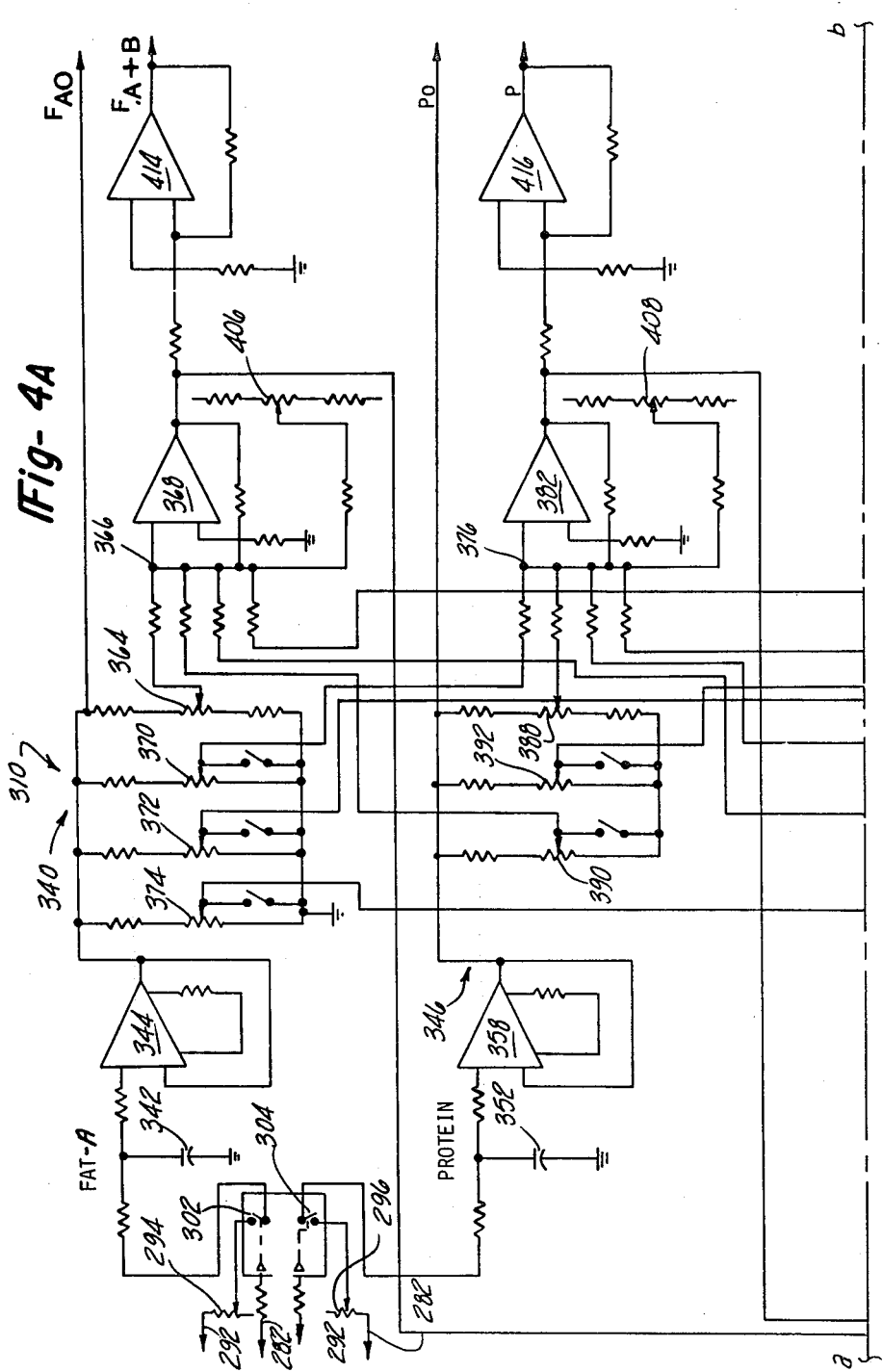

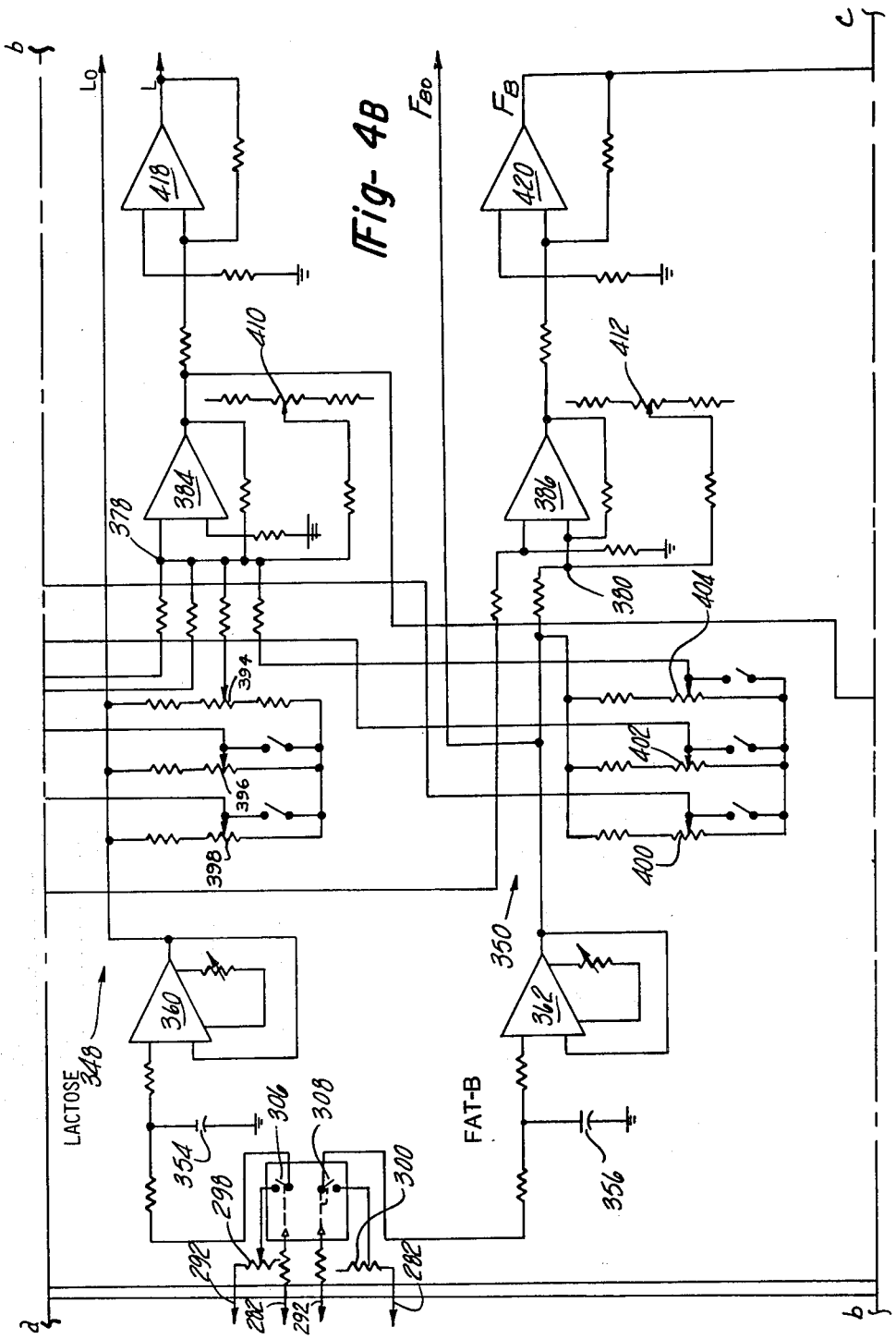

QUANTITATIVE MEASUREMENT OF FAT, PROTEIN AND LACTOSE IN DAIRY PRODUCTS

The present invention is directed to spectrophotometric analysis, and more particularly to methods and apparatus for quantitative measurement of fat, protein and lactose concentrations in dairy products employing infrared absorption techniques. Yet more specifically, the invention is directed to an improved method and apparatus for quantitative measurement of fat concentration in emulsions such as dairy products, including specifically milk.

Reference is made to the copending application of inventor-Shields herein, Ser. No. 84,662 filed Oct. 15, 1979 and now U.S. Pat. No. 4,310,763 entitled "Electro-optical Analyzer for Measuring Percentage by Weight of Fat, Protein and Lactose in Milk". Such copending application discloses and claims an apparatus for quantitative measurement of fat, protein, lactose, water, total solids and/or solids-non-fat in dairy products marketed under the trademark MULTISPEC by Berwind Corporation of Philadelphia, Penn. The disclosure of such copending application is incorporated herein by reference.

It is conventional in the art of infrared milk analysis quantitatively to measure the concentration of fat in the triglyceride carbonyl band at a wavelength of about 5.73 microns at which energy is absorbed by vibration at the ester linkages in the fat molecules. See, for example, U.S. Pat. No. 3,161,768. This technique yields satisfactory results so long as there is little variation in molecular weight of the fat or degree of lipolysis among the various samples. However, genetic variations among cow breeds and the practice of employing a variety of special feedstuffs such as protected tallow have caused sufficient variation in mean molecular weight of milk fat among differing herds that significant errors result when fat concentration is measured in the ester linkage absorption band.

It has also been known and heretofore proposed that the concentration of oily constituents in a sample, of which milk fat is one example, may be quantitatively measured employing infrared absorption techniques at the absorption band (about 3.48 microns) of stretching of the saturated carbon-hydrogen bonds. See Japanese published application No. 52-52694, Apr. 27, 1977. However, measurement of infrared absorption at the so-called carbon-hydrogen stretching band is subject to substantial variation due to variations in all natural fats, including milk or dairy fat, in molecular weight, degree of unsaturation and the number of hydroxy groups per molecule. As a result, use of the saturated carbon-hydrogen bond absorption band in place of the ester linkages absorption band in quantitative measurement fat concentration in milk, as proposed in U.S. Pat. No. 4,247,773, has not of necessity produced improved results, both because of variations in unsaturation, molecular weight and number of hydroxy groups as previously noted, and because the absorption in the carbon-hydrogen stretching region varies additionally with protein and lactose concentrations. In particular, significant errors have been noted employing this technique with skimmed samples. Furthermore, use of the saturated carbon-hydrogen absorption band is of little merit as applied to synthetic dairy products prepared with polyunsaturated vegetable oils, or to other types of natural oils which exhibit wide variations in molecular weight and degree of unsaturation, etc.

An object of the present invention is to provide improved method and apparatus for quantitatively measuring fat concentration in fat emulsions such as synthetic and natural dairy products, including specifically milk, which minimizes errors and inconsistencies previously described due to variations in fat molecular weight or degree of lipolysis.

Another and more specific object of the invention is to provide improved method and apparatus for quantitative measurement of fat, protein, lactose and/or solid concentrations in milk and milk products.

In summary, the foregoing and other objects of the invention are accomplished by application of the discovery that variations in infrared absorption in the carbon-hydrogen band and the ester linkage band due to variations in molecular weight and degree of lipolysis, etc. of fat emulsions are such that a more accurate determination of fat concentration may be obtained by assessing fat concentrations as a predefined conjoint function of both absorption readings. Most preferably, as applied to synthetic and natural dairy products and other natural fats, infrared absorption of peptide linkages in protein molecules at a wavelength of about 6.46 microns and of the hydroxy groups in lactose molecules at a wavelength of about 9.61 microns are combined with the carbon-hydrogen and ester linkage absorption measurements for determination of fat, protein and lactose concentrations by application of the various readings to a number of precalibrated scaling circuits for correcting each measurement reading due to absorption of the other constituents at the same wavelength. Solids concentration may also be obtained as a combined function of absorption in the carbon-hydrogen, ester, peptide and hydroxy bands.

In cases where there is considerable variation in the degree of unsaturation of the fat among the samples being analyzed, an accurate estimation of fat content would require a knowledge of the degree of unsaturation of the fat in each sample. This knowledge is obtainable either by a measurement of infrared absorbance at approximately 3.3 microns or some other wavelength capable of estimating degree of unsaturation, or by a separate determination of the iodine value (a measurement of degree of unsaturation) for the fat of each sample. If the measurement of degree of unsaturation is by infrared absorbance, the conjoint measurement of absorbance would include the absorbance at 3.3 microns or other wavelength, and the fat concentration would be assessed as a conjoint function of all of the measured absorbances. If the measurement of degree of unsaturation is by separate determination of iodine value, a preliminary assessment of fat concentration would be made as a conjoint function of the available absorbance. This would allow the calculation of equivalent iodine values for each sample for use in assessing concentration as a conjoint function of the measured absorbances and the equivalent iodine values. The latter calculation would be done repeatedly with re-adjustment of the equivalent iodine values between each successive estimation of fat. These repeated calculations can be done very quickly with preprogrammed calculators or computers.

The invention, together with additional objects, features and advantages thereof, will be best understood from the following description, the appended claims and the accompanying drawings in which:

Figure 1:
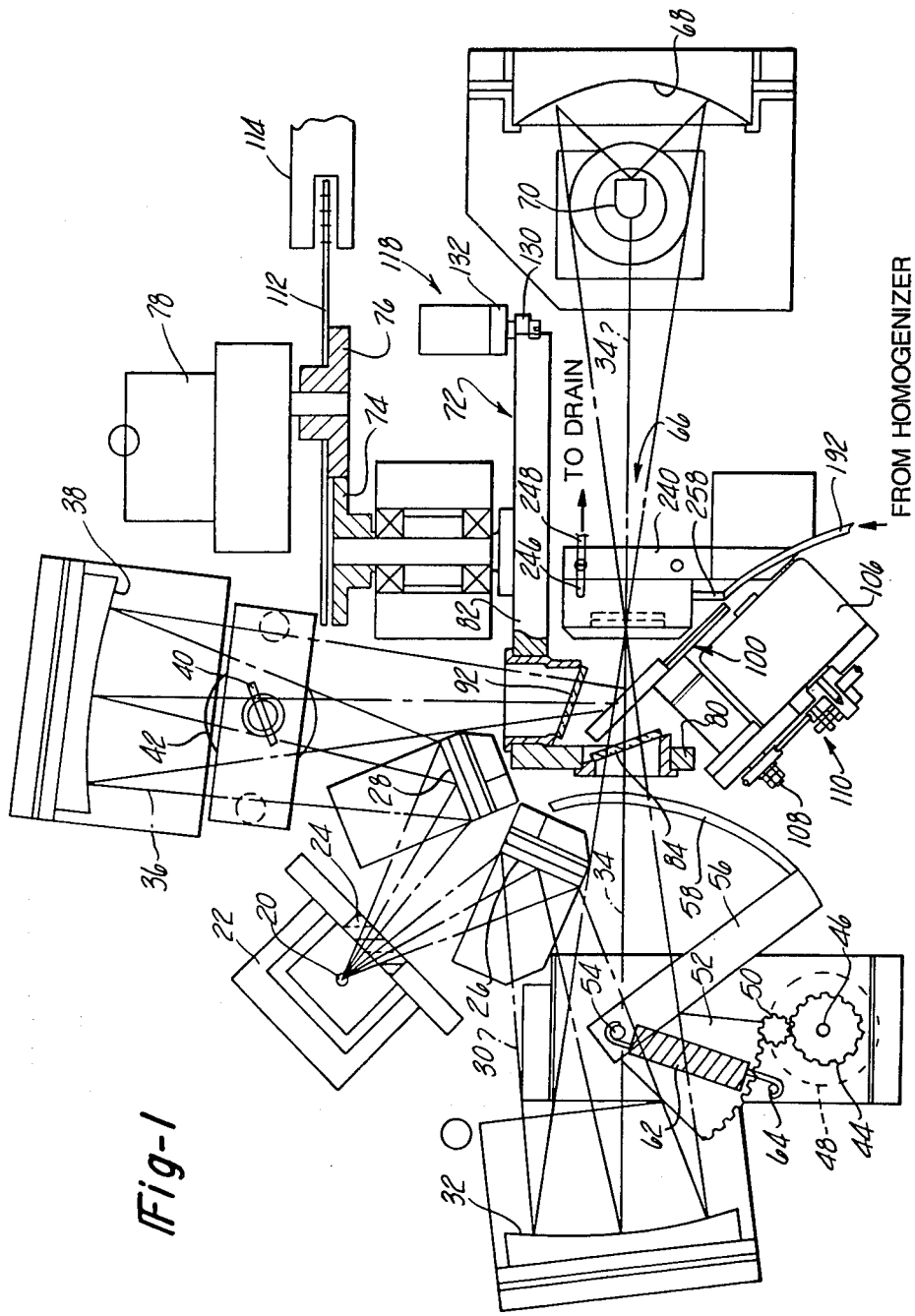
FIG. 1 is a top plan view of the optical portion of the MULTISPEC unit disclosed and claimed in the above-referenced Shields application in connection with which the subject invention is preferably employed.
Figure 2:
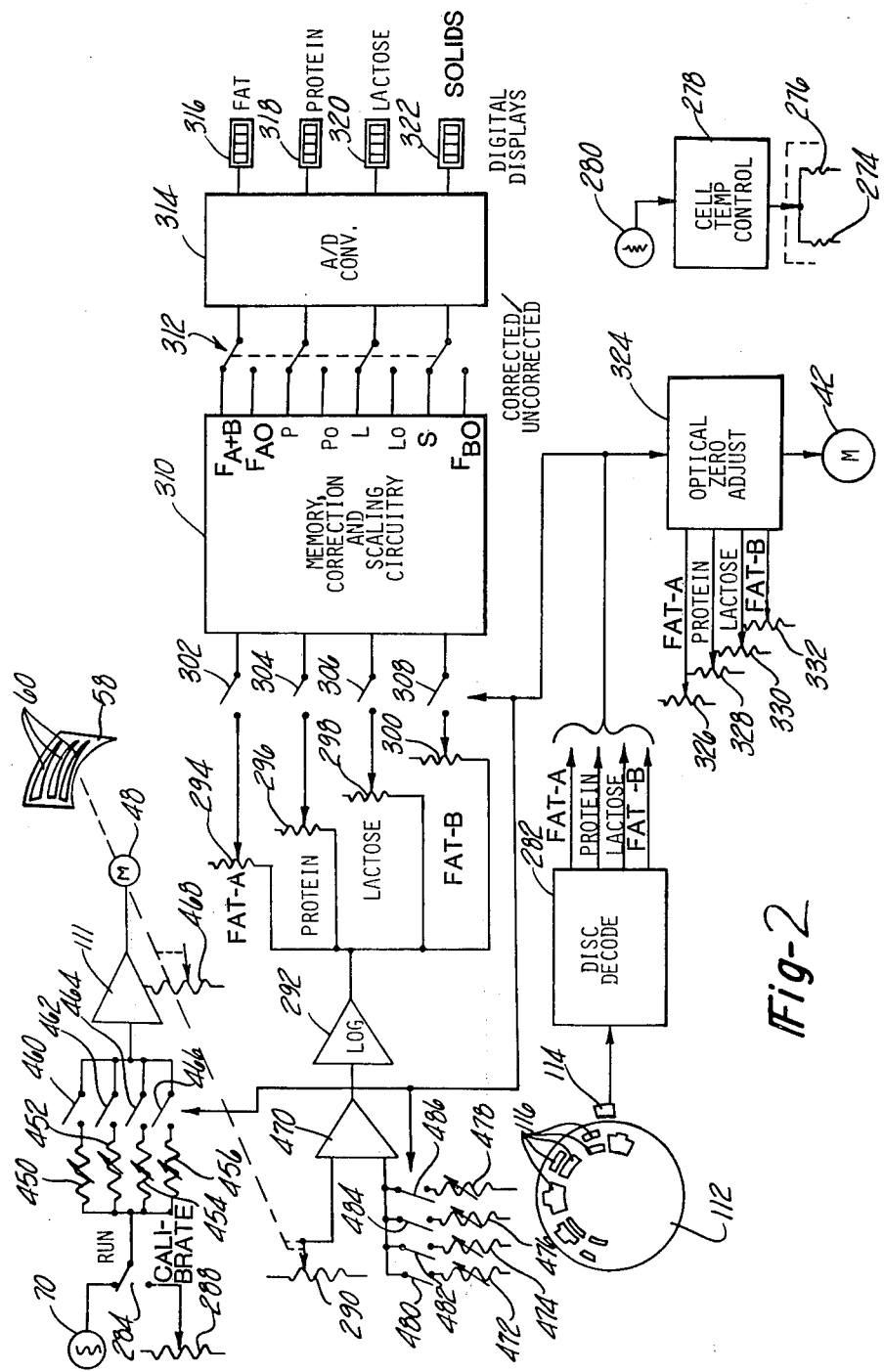
FIG. 2 is a functional block diagram of analysis electronics in accordance with the invention.
Figure 3:
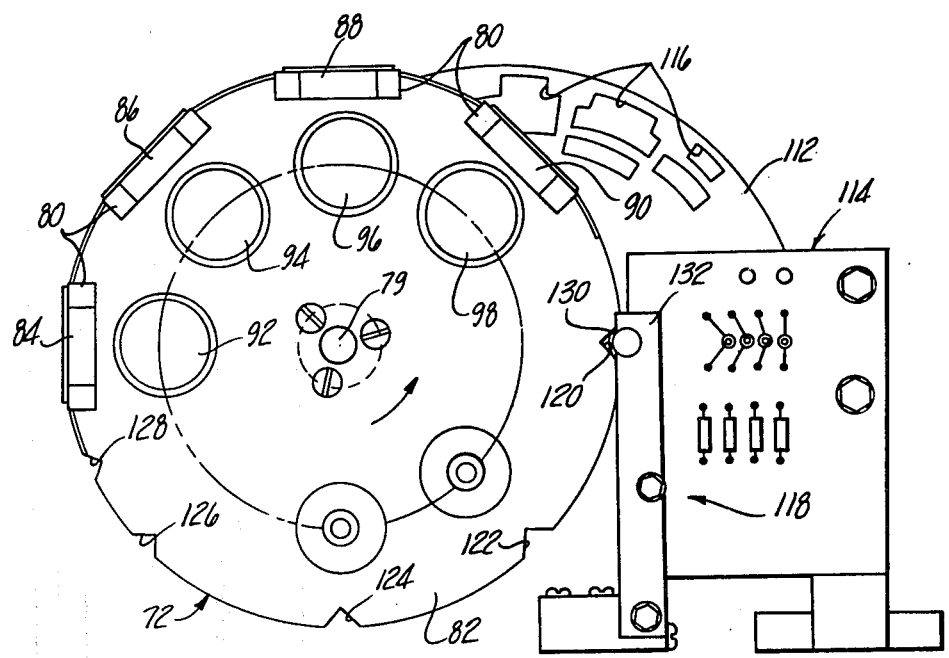
Figure 4C:
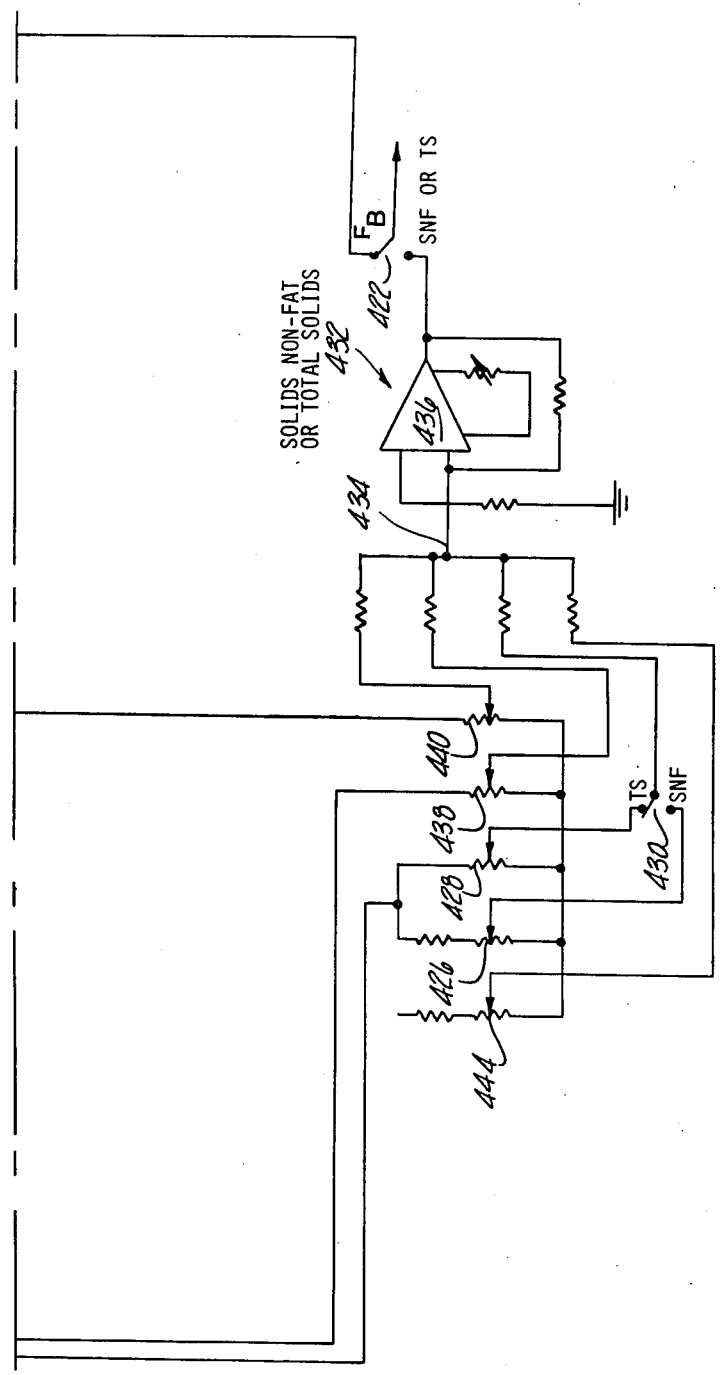

FIG. 3 is a side elevational view of the optical filter drum and coding disc assembly illustrated in FIG. 1; and FIGS. 4a-4c together comprise an electrical schematic diagram of the memory, correction and scaling circuitry illustrated in block form in FIG. 2, FIGS. 4a and 4b being interconnected along the lines a-b in each FIG., and FIGS. 4b and 4c being interconnected along the lines b-c in each FIG.

Referring to FIG. 1, the optical section or portion of the electro-optical milk analyzer disclosed in the above-referenced Shields application comprises a ceramic infrared energy source 20 enclosed within its own cooling chamber 22. An interference filter 24 having a preferred pass band in the range of three to ten microns is disposed in one wall of chamber 22 and transmits infrared energy from source 20 to a pair of plane mirrors 26,28 which operate to split the filtered infrared energy into diverging beams 30,36 illustrated in phantom lines in FIG. 1. The first or reference beam 30 is reflected by plane mirror 26 onto the surface of a spherical mirror 32 from whence reference beam 30 is focused onto an optical axis 34. The second or measurement beam 36 is reflected by plane mirror 28 onto the surface of a second spherical mirror 38 from whence the measurement beam is directed to intersect the reference beam from a direction orthogonal to beam axis 34. A sample cell generally indicated at 66 and described in greater detail in the above-referenced Shields application is disposed at the focus of reference beam 30 on beam axis 34. An ellipsoidal mirror 68 has a first focus at sample cell 66 and a second focus at a detector 70 for directing and concentrating the optical energy transmitted through sample cell 66 onto detector 70. Preferably, mirrors 26,28, 32,38 and 68 are of glass with highly reflecting surfaces of aluminum or gold.

An upstanding vane or shutter 40 is disposed in the path of measurement or reference beam 36 or 30 (drawing shows vane in measurement beam), and is rotatably coupled to a motor 42 for a purpose to be described hereinafter. A drive gear 44 is coupled to the shaft 46 of a servomotor 48 through a slipping clutch mechanism (FIG. 1 and schematically in FIG. 2) and through the idler gear 50 to a gear section 52 mounted to pivot in the plane of FIG. 1 about the pin 54. An arm 56 is rigidly coupled to gear section 52 and has a comb or shutter 58 (FIGS. 1 and 2) carried on the pivot-remote end thereof for adjustable placement within the path of reference beam 30 between mirror 32 and sample cell 66 as controlled by servomotor 48. Comb 58 is arcuate in cross section with a radius centered on the axis of pivot pin 54 and, as best seen in FIG. 2, possesses a plurality of transversely spaced longitudinal slots 60 each having a width which varies linearly with arcuate comb length. Thus, reference beam 30 is selectively attenuated as a linear function of the degree or extent to which comb 58 is inserted into the beam. Comb 58 is preferably coated with material which absorbs infrared energy. A coil spring 62 (FIG. 1) extends between arm 56 and a fixed stanchion 64 for resiliently biasing gear drive chain or transmission 44,50,52 so as to achieve substantially zero backlash. Coupled to gear 50 is an accurately linear potentiometer (schematically at 290 in FIG. 2) arranged to provide a voltage to measuring circuits which is proportional to the percentage transmission (%T) of the sample. A second potentiometer (schematically at 468 in FIG. 3) coupled to the same spindle within the same potentiometer housing provides velocity feedback for the servomotor drive circuit.

A filter wheel 72 shown in FIGS. 1 and 3 comprises a drum coupled by the gears 74,76 to a drive motor 78 to rotate about a fixed axis 79 (FIG. 3) orthogonal to reference beam axis 34. Drum 72 includes segmented circumferential rim portions 80 which intersect reference beam 30 between comb 58 and cell 66 as drum 72 is rotated, and an axially facing disc portion 82 which intersects measurement beam 36. First and second series of optical absorption-type filters are respectively disposed in rim portion 80 and disc portion 82 of drum 72, and are grouped in coordinated pairs on corresponding radii from the axis of rotation 79 such that one filter in each filter pair simultaneously intersects associated ones of the reference and measurement beams 30,36. More particularly, four circumferentially spaced reference filters 84,86,88,90 are mounted in associated segments of drum rim portion 80 sequentially to intersect reference beam 30 as drum 72 is rotated in the counterclockwise direction as viewed in FIG. 3. In a particularly preferred application of the invention for analysis of fat, protein, lactose and solid concentrations in milk, reference filters 84-90 preferably possess nominal peak transmission wavelengths of 5.55 (fat-A), 6.68 (protein), 7.67 (lactose) and 3.56 (fat-B) microns respectively. A series of circumferentially spaced measurement filters 92,94,96 and 98 are disposed on the planar disc portion 82 of drum 72 in radially aligned association with respective reference filters 84,86,88 and 90 as best seen in FIG. 3. For analysis of fat, protein, lactose and solids in milk, filters 92,94,96 and 98 preferably possess nominal peak transmission wavelengths of 5.72 (fat-A), 6.46 (protein), 9.6 (lactose) and 3.48 (fat-B) microns respectively. Preferably, at least fat measurement filter 84 is tiltably mounted (by means not shown) so as to facilitate factory fine-tuning of the peak transmission wavelength to the values indicated.

It will be apparent that the wavelengths denominated "fat-A" correspond to the so-called triglyceride carbonyl or ester linkage band previously discussed, while the wavelengths denominated "fat-B" correspond to the so-called saturated carbon-hydrogen band. Similarly, the "protein" wavelengths correspond to the absorption wavelength of peptide linkages, while the "lactose" wavelengths correspond to the absorption peak of hydroxy groups in the lactose molecules.

A detent locking arrangement 118 is provided for holding drum 72 in fixed rotational position with a filter pair in the associated beam paths. Detent 118 comprises a series of five V-shaped notches 120,122,124, 126 and 128 (FIG. 3) disposed about the periphery of drum disc portion 82. Notches 120,122,124 and 126 are respectively diametrically opposed to filter pairs 84,92; 86,94;88,96; and 90,98. Notch 128 is for holding drum 72 in a rest position. A roller bearing 130 is rotatably mounted in the plane of a drum axis 79 on a spring-biased pivot arm 132 for resiliently engaging the respective detents as drum 72 is rotated. Thus, in the position illustrated in FIG. 3, bearing 130 resiliently engages notch 120 to hold fat-A reference and measurement filters 84,92 in reference and measurement beams 30,36 (FIG. 1). When drum 72 is rotated to the next position wherein bearing 130 engages notch 122, protein reference and measurement filters 86,94 are held in the beam paths. Notch 124 operates in conjunction with lactose reference and measurement filters 88,96, and notch 126 operates in conjunction with fat-B reference and measurement filters 90,98 in a similar manner.

A program or code disc 112 (FIGS. 1 and 3) is mounted on gear 76 and is thereby rotatably coupled to filter drum 72 such that a peripheral portion of disc 112 passes through the optical sensor generally indicated at 114 in FIG. 1 as a function of drum rotation. Optical sensor 114 is responsive to peripheral apertures 116 (FIG. 3 and schematically in FIG. 2) in disc 112 for controlling system electronics (FIG. 2) to stop rotation of drum 72 when a selected filter pair is disposed in the corresponding beams, to control the electronics for measurement of the particular constituent with which the filter pair is associated and to switch the pump motor on at the correct point in the operation cycle. Provision of interference filter 24 adjacent infrared source 20 (FIG. 1) for passing only a portion (three to ten microns) of the infrared spectrum of interest to the absorption-type reference and measurement filters reduces heating of the latter and improves accuracy of the overall apparatus.

A chopper shutter or disc 100 (FIG. 1) is positioned at the zone of intersection between reference beam 30 and measurement beam 36 at an orientation of 45° with respect to both beam axes. As best seen in FIG. 1, disc 100 is angled to nest within the angle formed by drum rim and disc portions 80,82. Disc 100 comprises a semicircular aperture 102 and a semicircular reflective portion 104 alternately positioned in the paths of beams 30,36 at the point of intersection therebetween as disc 100 is rotated by the motor 106 coupled to the disc drive shaft 108 by the belt and pulley arrangement generally indicated at 110 in FIG. 1. Thus, disc 100 nested within the rim and disc portions of drum 72 is operative alternately to direct the measurement and reference beams through sample cell 66 onto detector 70.

Thus, rotation of disc 100 at the preferred frequency of 12.5 hertz (50 hertz mains frequency) or 15 hertz (60 hertz mains frequency) operates to transmit to detector 70 a composite beam which alternates in intensity as a function of the difference in percentage transmission of a sample in cell 66 at the particular wavelengths transmitted by whichever reference and measurement filters are in the beam paths. Detector 70 produces a signal which is amplified and conditioned by amplifier 111 and associated circuitry (FIG. 2) to drive servomotor 48 (FIGS. 1 and 2). This positions comb 58 within beam 30 so as to minimize this intensity differential. In this manner, the ultimate position of the servomotor 48, and the potentiometer coupled to it, for any filter pair, is proportional to the change in transmission of the sample situated in cell 66 at the wavelengths transmitted by that filter pair.

Sample cell 66, chopper disc 100, and the fluid flow system, including a homogenizer and drive pump, for supplying milk to cell 66 are all disclosed in detail in the above-referenced copending Shields application, which disclosures are incorporated herein by reference.

Heating resistors 274,276 (FIG. 2) are mounted on the sample cell and are connected to appropriate control circuits 278 for maintaining the temperature of sample cell assembly 66 at a selected temperature above instrument temperature. For analysis of milk, a cell temperature of 40°±0.2° C. is preferred. Temperature control circuit 278 may comprise a suitable bridge circuit or the like responsive to a thermistor 280 (FIG. 2) mounted on the sample cell. Similar temperature control structure is preferred in connection with the homogenizer. Preferably, the homogenizer is physically located closely adjacent to cell 66 but external to the optics unit, and test measurements are performed a short time after fluid sample is placed in the cell so that the homogenized fat particles in the milk do not have an opportunity to form aggregates.

Instrument measuring and control circuits are illustrated in functional block form in FIG. 2 and include decoding circuitry 282 responsive to coded apertures 116 in program disc 112 through optical sensor 114 for indicating which of the filter pair on drum 72 is in the beam paths, and thereby controlling the remainder of the circuits for measurement of fat, protein, lactose and solids concentrations. Detector 70 is connected through the normally closed contacts of a run/calibrate switch 284 to the input of amplifier 111, which is a.c. coupled and tuned to $12.5\pm3$ Hz (for 50 hertz line frequency) or to $15\pm3$ Hz (for 60 hertz line frequency). Connection of detector 70 to amplifier 111 is through one of four variable resistors 450–456 (selected through switches 460–466 by photoposition decoding circuitry 282 for fat-A, protein, lactose and fat-B respectively) which determines the servo amplifier voltage gain and hence sensitivity to the detector signal voltage for each component being measured. The amplifier output drives servomotor 48 which controls the comb position.

A voltage derived from the potentiometer 468 coupled to the comb mechanism provides velocity feedback to amplifier 111 insuring a controlled rate of comb movement. Also coupled to the comb mechanism is the precision potentiometer 290. Thus, a voltage directly proportional to comb position is provided to an input of amplifier 470. Summed to this amplifier is a voltage derived from one of four preset adjustable resistors 472–478 selected through switches 480–486 by photoposition decoding circuitry 282 for fat-A, protein, lactose and fat-B respectively. This provides a bias to the comb position voltage prior to logging by log amplifier 292. Adjustment of the bias allows the output of the log amplifier 292 to be linear for equal increments of concentration of the component being measured in the cell in accordance with Beer's law. Beer's law is: $D = \ln 1/T$ for D equals optical density, T equals percent transmission and ln indicates the taking of the natural logarithm (base e).

The sequential concentration signals from log amplifier 292 are fed by slope control resistors 294–300 through switches 302–308 controlled by disc decode circuitry 282 to a four-channel memory, correction and scaling circuit 310 which will be described in greater detail in connection with FIG. 4. Circuit 310 provides at its output a series of uncorrected signals $F_{AO}$, $P_O$, $L_O$ and $F_{BO}$ for fat-A, protein, lactose and fat-B respectively, and a second series of signals $F_{A+B}$, P, L and S which have been cross-corrected for effects due to change in absorption of infrared energy at the particular test wavelengths selected for the others. The outputs of circuit 310 are connected through a four-pole double-throw switch generally indicated at 312 for selecting either corrected or uncorrected signals, and through a four-channel a/d converter 314 to digital readouts 316,318,320 and 322 for indicating concentration in percentage by weight of fat, protein, lactose and solids respectively. Displays 316–322 preferably comprise decimal displays.

The decoded outputs of circuit 282 are additionally connected to an optical zero adjustment circuit 324 which controls the position of vane 40 (FIG. 1) by means of motor 42. Zero adjust circuit 324 receives second control inputs from the manually adjustable resistors 326,328,330 and 332 for placing vane 40 (FIG. 1) in the desired zero adjustment position for fat-A, protein, lactose and fat-B respectively. Calibration of zero adjustment circuit 324 and of memory, correction and scaling circuit 310 will be discussed in greater detail hereinafter. It will be appreciated, of course, that the various resistors illustrated in FIG. 2 (and in FIG. 4 yet to be described) are to be connected to appropriate biasing voltages such as +12 volts, −12 volts and zero volts.

Referring now to FIGS. 4a–4c, memory correction and scaling circuitry 310 illustrated therein basically comprises four circuit channels 340,346,348 and 350 (FIGS. 4a–4b) labeled for providing corrected and uncorrected indications of fat, protein and lactose concentrations, and a fifth channel 432 (FIG. 14c) for deriving an indication of non-fat solid concentration or total solid concentration from signals available in the other four channels. Fat-A channel 340 receives an input signal from adjustable scaling resistor 294 (FIGS. 2 and 4a) through switch 302, which preferably comprises an FET switch controlled by disc decode electronics 282 as previously described. The switched input signal is fed and stored on a capacitor 342 across the input of a high impedance input current amplifier 344 which provides at its output the uncalibrated fat signal $F_{AO}$. Similarly, protein, lactose and fat-B channels 346,348 and 350 each include a corresponding storage capacitor 352,354 and 356 connected across the input of the high impedance input amplifiers 358,360 and 362 for providing uncorrected protein, lactose and water signals $P_O, L_O$ and $F_{BO}$ respectively.

The output of fat input amplifier 344 is connected in fat channel 340 through an adjustable resistor 364 to a summing junction 366 at the input of second stage amplifier 368. The output of amplifier 344 is also connected through the adjustable resistors 370 and 372 to the summing junctions 376 and 378 at the inputs of second stage amplifiers 382 and 384 in protein and lactose channels 346 and 348, and through the adjustable resistor 374 to one input of the second stage amplifier 386 in fat-B channel 350. The output of protein input amplifier 358 is connected through an adjustable resistor 388 to protein summing junction 376, through a second adjustable resistor 390 to fat summing junction 366, and through a third adjustable resistor 392 to lactose summing junction 378. The output of lactose input amplifier 360 is connected through a first adjustable resistor 394 to lactose summing junction 378, through a second adjustable resistor 396 to protein summing junction 376, and through a third adjustable resistor 398 to fat-A summing junction 366. The output of fat-B input amplifier 362 is fed to a summing junction 380 at a second input of second stage amplifier 386, to fat-A summing junction 366 through the adjustable resistor 400, to protein summing junction 376 through adjustable resistor 402 and to lactose summing junction 378 through the adjustable resistor 404. Summing junctions 366,376,378 and 380 are additionally connected to the adjustable resistors 406,408,410 and 412 respectively.

Second stage amplifier 368 in fat-A channel 340 is connected through an output amplifier 414 for providing an analog signal (voltage) $F_{A+B}$ as a linear function of fat concentration and corrected for cross-absorption effects as previously described. Similarly, protein and lactose second stage amplifiers 382 and 384 are connected through corresponding output amplifiers 416 and 418 for providing corrected analog protein and lactose signal (voltages) P and L. The output of amplifier 386 in fat-B channel 350 is connected through an output amplifier 420 to one selectable contact of a switch 422 which selects either fat-B concentration $F_B$ or one of the solid concentrations TS (total solids) or SNF (solids non-fat) for display on digital readout 322 (FIG. 2). The output of second stage amplifier 368 in fat-A channel 340 is additionally connected to solid channel 432 through the adjustable resistors 426 and 428 to the two selectable contacts of a switch 430 for choosing TS or SNF for display. The common contact of switch 430 is connected to a summing junction 434 at the input of an amplifier 436. The output of second stage amplifier 382 in protein channel 346 is connected through an adjustable resistor 438 to solid summing junction 434. The output of lactose second stage amplifier 384 is connected through the adjustable resistor 440 to junction 434. An adjustable resistor 444 provides an offset voltage to compensate in the solids and solids non-fat readout for the average value of minearl matter in milk. The wipers of adjustable resistors 370,372 and 374 in fat-A channel 340, 390 and 392 in protein channel 346, 396 and 398 in lactose channel 348 and 400,402 and 404 in fat-B channel 350 have normally open switches connected thereacross to ground for short circuiting the respective adjustable resistors during the calibration operation to be described.

Corrected signals for fat $F_{A+B}$, protein P, lactose L, total solids TS and solids non-fat SNF are given by the following equations:

$$F_{A+B} = aF_{AO} + bP_O + cL_O + dF_{BO} + e$$

$$P = fF_{AO} + gP_O + hL_O + iF_{BO} + j$$

$$L = kF_{AO} + mP_O + nL_O + OF_{BO} + p$$

$$TS = sF_{A+B} + tP + uL + v$$

$$SNF = wF_{A+B} + tP + uL + v$$

wherein the coefficients a–w are predetermined empirically and are adjusted by the variable resistors in FIGS. 14a–14c.

| coefficient | calibrated by variable resistor |
|---|---|
| a | 364 |
| b | 390 |
| c | 398 |
| d | 400 |
| e | 406 |
| f | 370 |
| g | 388 |
| h | 396 |
| i | 402 |
| j | 408 |
| k | 372 |
| m | 392 |
| n | 394 |
| o | 404 |
| p | 410 |
| s | 428 |

| coefficient | calibrated by variable resistor |
|---|---|
| t | 438 |
| u | 440 |
| v | 444 |
| w | 426 |

The values of coefficients a–w depend upon the characteristics of the filters and vary a great deal from one filter batch to another.

Before discussing overall operation of the invention, the method of calibration will be briefly described. First, referring to FIGS. 1 and 3, the pump (not shown) is operated to draw water, preferably distilled water, into the homogenizer and pulse water through the fluid system to purge the homogenizer, the various conduits and sample cell 66. A "sample" of water is left in the sample cell. Servomotor 48 is turned on and switch 312 (FIG. 2) is in the uncorrected position. Filter drum 72 (FIG. 1) is then operated sequentially to place the fat-A, protein, lactose and fat-B filter pairs in the respective optical beams. With the fat-A filters in the beams, for example, and chopper 100 energized such that radiation is incident on detector 70 as an alternating function of the intensity of the sample and reference beam passing through the sample cell, resistor 326 (FIG. 2) is adjusted until the arcuate comb 58 is in an arbitrary "zero" position which yields a "zero" reading at display 316. As resistor 326 is adjusted, vane 40 (FIG. 1) is correspondingly adjusted to selectively attenuate measurement beam 36 so that the measurement and reference beams at 5.73 and 5.55 micron wavelength respectively are equal in intensity at detector 70. This procedure is then repeated for protein, lactose and fat-B channels successively, such that resistors 328,330 and 332 (FIG. 2) are adjusted to correspond to zero positions for each of these measurements respectively. Thereafter during measurement operations, optical zero adjust circuitry 324 (FIG. 2) will automatically rotate vane 40 by means of motor 42 to the adjusted zero position depending upon the constituent to be measured.

With switches 430 and 422 (FIG. 4c) in the TS or total solids position, servomotor 48 (FIG. 2) is disconnected (by switch means not shown) and resistor 444 (FIG. 4c) is adjusted until the reading on display 322 (FIG. 2) is equal to the sum of displays 316,318 and 320. With servo 48 off, filter drum 72 is then rotated to the fat-A position and resistor 294 (FIGS. 2 and 4a) is adjusted while switch 312 is sequentially switched back and forth between corrected and uncorrected positions until the corrected ($F_{A+B}$) and uncorrected ($F_{AO}$) fat signals indicated at readout 316 are identical. The same procedure is then repeated for protein, lactose and fat-B channels such that adjustable resistors 294–300 are in their calibrated positions.

Drum 72 is then again returned to the fat-A position and switch 284 (FIG. 2) is placed in the calibrate position wherein servo amplifier 286 is connected to adjustable resistor 288. Servomotor 48 is re-energized and resistor 288 is adjusted until digital display 316 reads "10.00" with switch 312 in the uncorrected position. The switches across adjustable resistors 370,372 (FIG. 4a) are open and the remaining switches across the various adjustable resistors in FIG. 4 are closed. Resistors 364,370 and 372 are then adjusted while switch 312 (FIG. 2) is alternately switched between corrected and uncorrected positions until the corrected fat signal $F_{A+B}$ equals 10a, i.e. $aF_{AO}$, the corrected protein signal equals the uncorrected P signal ($P_O$) plus 10f and the corrected lactose signal equals the uncorrected signal $L_O$ plus 10k. Filter drum 72 (FIG. 1) is then moved to the protein position and resistor 288 is adjusted to yield an uncorrected signal $P_O$ on display 318 of "10.00". The switches across adjustable resistors 390,392 (FIG. 4a) are opened and the remaining resistor-bridging switches in FIG. 4 are closed. Resistors 388,390 and 392 are then adjusted while switch 312 (FIG. 2) is alternately switched between corrected and uncorrected positions until the corrected protein signal on display 318 is equal to 10g, i.e. $gP_O$, the corrected fat signal at display 316 is equal to the display at the uncorrected position of switch 312 plus 10b and the corrected lactose signal at display 320 is equal to the signal in the uncorrected position of switch 312 plus 10m.

Drum 72 is then rotated to the lactose position and resistor 288 is adjusted to yield an uncorrected lactose signal at display 320 of "10.00". The switches bridging resistors 396 and 398 (FIG. 4b) are opened and the remaining resistor-bridging switches in FIG. 14 are closed. Resistors 394,396 and 398 are then adjusted while switch 312 (FIG. 3) is alternately switched between corrected and uncorrected positions until the corrected lactose signal at display 320 is equal to 10n, the corrected fat signal at display 316 is equal to the signal when switch 312 is in the uncorrected position plus 10c and the corrected protein signal at display 318 is equal to the signal when switch 312 is in the uncorrected position plus 10h.

Drum 72 is then rotated to the fat-B position and resistor 288 is adjusted to yield an uncorrected fat-B signal at display 322 of "10.00". The switches bridging resistors 400 and 402 (FIG. 4b) are opened and the remaining resistor-bridging switches in FIG. 4 are closed. Resistors 400 and 402 are then adjusted while switch 312 (FIG. 2) is alternately switched between corrected and uncorrected positions until the corrected fat signal at display 316 is equal to the signal when switch 312 is in the uncorrected position plus 10d, the uncorrected protein signal at display 318 is equal to the signal when switch 312 is in the uncorrected position plus 10i, and the uncorrected lactose signal at display 320 is equal to the signal when switch 312 is in the uncorrected position plus 10o.

Servomotor 48 is then turned off. All resistor-bridging switches in FIG. 4 are closed and switch 312 is placed in the uncorrected position. Resistor 444 (FIG. 14c) is then re-adjusted until the display at 322 is equal to the sum of the displays at 316–320 plus the required correction constant v.

Constants e, j and p are not required when the instrument is set up for analysis of whole milk. It is, however, visualized that for certain applications to dairy product analysis, as well as more general applications to other types of fat emulsions, both natural and synthetic, it may be necessary to include an intercept adjustment. In such cases this can be effected in fat, protein and lactose channels by adjustments to resistors 406,408 and 410. The value of these constants or intercepts will be indicated by the calibration data for the appropriate component.

With all adjustments made, the embodiment of the invention hereinabove described is now ready for operation. A specimen of milk to be tested is placed within the sample cell. Filter drum 72 is then activated sequentially to stop at the fat-A protein, lactose and fat-B positions. In the fat-A position, reference and measurement beams are alternately directed through the sample cell 66 onto the detector 70 which, in turn, operates servomotor 48 to position comb 60 within reference beam 30 (FIG. 1) until the reference and measurement beams seen by the photocell are equal in intensity. The signal on resistor 290 (FIG. 2) indicative of fat-A concentration is then stored on capacitor 342 (FIG. 4a). This process is repeated in the protein, lactose and fat-B positions of filter drum 72. Corrected fat, protein and lactose concentrations in percent are then displayed at 316–320. If total solids or solids non-fat is desired, switch 422 is placed in the alternate position and switch 430 is placed in the desired position such that percentage of total solids or solids non-fat is automatically provided at display 322. The specimen may then be changed and the cycle repeated as desired.

The invention claimed is:

1. Apparatus for measuring fat concentration in fat emulsions such as natural and synthetic dairy products comprising means for holding a product sample, means for irradiating said sample with energy in the infrared spectrum at a first wavelength characteristic of ester linkages and a second wavelength characteristic of saturated carbon-hydrogen bonds, and means for assessing fat concentration in the sample as a predetermined conjoint function of energy absorbed by said sample at both said first and second wavelengths.

2. The apparatus set forth in claim 1 wherein said irradiating means includes means for successively irradiating said sample at said first and second wavelengths.

3. The apparatus set forth in claim 1 or 2 further comprising means for irradiating said sample with energy at a third wavelength characteristic of peptide linkages and a fourth wavelength characteristic of hydroxy groups in the sample, and means coupled to said assessing means and responsive to absorption of energy at said third and fourth wavelengths for correcting said predetermined conjoint function for absorption due to said peptide linkages and hydroxy groups at said first and second wavelengths.

4. The apparatus set forth in claim 3 further comprising means for indicating protein and lactose concentrations in said sample as a function of absorption of energy at said third and fourth wavelengths.

5. A method of measuring fat concentration in dairy products comprising the steps of irradiating a test sample with infrared energy, determining infrared absorption of said sample at a first wavelength characteristic of carbon-hydrogen bonds and a second wavelength characteristic of ester linkages, and then quantitatively assessing the fat concentration of said sample as a predetermined function of absorption at both said first and second wavelengths.

6. The method set forth in claim 5 comprising the additional steps of determining infrared absorption of said sample at a third wavelength characteristic of peptide linkages and a fourth wavelength characteristic of hydroxy groups, and assessing said fat concentration as a predetermined function of absorption at all of said first, second, third and fourth wavelengths.

7. The method set forth in claim 6 comprising the additional step of assessing solids concentration in said sample as a predetermined function of absorption at all of said wavelengths.

* * * * *